(12) United States Patent
Hwang et al.

(10) Patent No.: US 6,451,815 B1
(45) Date of Patent: Sep. 17, 2002

(54) METHOD OF ENHANCING BIOAVAILABILITY OF FEXOFENADINE AND ITS DERIVATIVES

(75) Inventors: Kin-Kai Hwang, Overland Park, KS (US); Dennis H. Giesing, Lee's Summit, MO (US); Gail H. Hurst, Stilwell, KS (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/353,462

(22) Filed: Jul. 13, 1999

Related U.S. Application Data

(63) Continuation of application No. 09/129,713, filed on Aug. 5, 1998, now abandoned.
(60) Provisional application No. 60/090,103, filed on Aug. 14, 1997.

(51) Int. Cl.$^7$ .............................................. A61K 31/445
(52) U.S. Cl. ....................................... 514/317; 514/946
(58) Field of Search .................................. 514/317, 946

(56) References Cited

U.S. PATENT DOCUMENTS

| | | |
|---|---|---|
| 4,254,129 A | 3/1981 | Carr et al. |
| 4,285,957 A | 8/1981 | Carr et al. |
| 5,567,592 A | 10/1996 | Benet et al. |
| 5,574,045 A | 11/1996 | Ortyl et al. |
| 5,665,386 A | 9/1997 | Benet et al. |
| 5,716,928 A | 2/1998 | Benet et al. |

FOREIGN PATENT DOCUMENTS

| | | |
|---|---|---|
| WO | 9520982 | 8/1995 |
| WO | 9640192 | 12/1996 |

OTHER PUBLICATIONS

Germann et al., Cell Biology, vol. 4, 1993: pp. 63–76.
Chang et al., Clinical Pharmacology & Therapeutics, Mar. 1996, pp. 297–303.
Saitoh et al., Pharmaceutical Research, vol. 12, No. 9, 1995, pp. 1304–1310.
Nerurkar et al., Pharmaceutical Research, vol. 13, No. 4, 1996, pp. 528–534.
Cordon–Cardo et al., J. of Histochemistry and Cytochemistry, vol. 38, No. 9, 1990, pp. 1277–1287.
Wacher et al., Molecular Carcinogenesis 13, 1995 pp. 129–134.
Yun et al. Drug Metabolism and Disposition, vol. 21, No. 3, 1993, pp. 403–409.
Ling et al. Drug Metabolism and Disposition, vol. 23, No. 6, 1995, pp. 631–636.
Bendetti et al., Drug Metabolism Reviews, 1999; 31(3):665–717.

*Primary Examiner*—James H. Reamer
(74) *Attorney, Agent, or Firm*—Jiang Lin; Charlotte L. Barney

(57) ABSTRACT

The present invention relates to a method of enhancing the bioavailability of a piperidinoalkanol antihistamine in a patient which comprises co-administering to said patient an effective antihistaminic amount of said piperidinoalkanol and an effective p-glycoprotein inhibiting amount of a p-glycoprotein inhibitor.

30 Claims, No Drawings

METHOD OF ENHANCING BIOAVAILABILITY OF FEXOFENADINE AND ITS DERIVATIVES

This is a continuation application which is a continuation of application Ser. No. 09/129,713 filed Aug. 5, 1998 now abandoned which claims priority of U.S. Provisional Application Ser. No. 60/090,103 filed Aug. 14, 1997.

BACKGROUND

The term "multidrug resistance" (MDR) describes the phenomenon whereby certain cancerous tumor cells develop a resistance to broad classes of cytotoxic agents when exposed to an individual cytotoxic agent. In other words, after a certain period of treatment with a cytotoxic agent which initially shows efficacy in controlling the growth of the tumor, the tumor develops a resistance not only to the specific agent to which the tumor was exposed, but also to broad classes of structurally and functionally unrelated agents. It has recently been found that MDR tumor cells over express a particular membrane glycoprotein known as p-glycoprotein ("p" for permeability). This p-glycoprotein is a member of the superfamily of ATP-binding cassette (ABC) transporters. It is thought that the exposure of the MDR tumor cells to a cytotoxic agent causes the induction of this p-glycoprotein which mediates a reverse transport system located on the tumor cell membrane that pumps the cytotoxic agent, as well as the other broad classes of cytotoxic agents, out of the tumor cell thus providing mutiple drug resistance for the cell.

P-glycoprotein is not just found in tumor cells. It is also expressed in a variety of normal, non-cancerous, epithelial and endothelial cells including in such tissues as the adrenal cortex, in the brush border of the proximal renal tubule epithelium, on the lumenal surface of biliary hepatocytes, in pancreatic ductules, and in the mucosa of the small and large intestine. For purposes of describing the present invention, the presence of p-glycoprotein in the small and large intestine is of particular interest.

When substances are ingested, they are mixed with digestive substances secreted by the body and are ultimately combined in a mixture in the lumen of the intestine. The lumen of the intestine is in contact with certain special epithelial cells which form the mucosa of the intestine or the intestinal wall. Nutrients and other substances present in the intestinal lumen passively diffuse into these intestinal epithelial cells and later diffuse into the portal circulation which carries the nutrients via the blood stream on to the liver. Thus, nutrients and other substances are absorbed into the body and become bioavailable for use by other tissues in the body.

The intestinal epithelial cells, however, do not just operate as a vehicle for passive diffusion of nutrients and other ingested substances. In addition, there are various active transport mechanisms located in the outer membrane of the epithelial cells which actively transport various nutrients and other substances into the cell. It is now thought that one of the active transport mechanisms present in the intestinal epithelial cells is p-glycoprotein transport mechanism which facilitates the reverse transport of substances, which have diffused or have been transported inside the cell, back into the lumen of the intestine. It has been speculated that the p-glycoprotein present in the intestinal epithelial cells may function as a protective reverse pump which prevents toxic substances which have been ingested and diffused or transported into the epithelial cell from being absorbed into the circulatory system and becoming bioavailable. One of the unfortunate aspects of the function of the p-glycoprotein in the intestinal cell however is that it can also function to prevent bioavailability of substances which are beneficial, such as certain drugs which happen to be substates for the p-glycoprotein reverse transport system.

It has now been found that, surprisingly, the antihistamines of the present invention are coincidentally also targeted by the p-glycoprotein reverse transport system in intestinal epiothelial cells and therefore are not fully bioavailable. The present invention successfully provides a method for enhancing the bioavailablilty of these antihistamines.

SUMMARY IF THE INVENTION

The present invention relates to a method of enhancing the bioavailability of a piperidinoalkanol antihistamine of Formula I

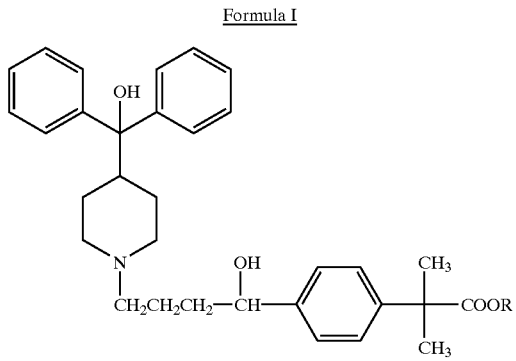

Formula I wherein

R is hydrogen or $C_1$–$C_6$ alkyl, or a pharmaceutically acceptable salt or an individual optical isomer thereof, in a patient which comprises co-administering to said patient an effective antihistaminic amount of said piperidinoalkanol and an effective p-glycoprotein inhibiting amount of a p-glycoprotein inhibitor. The present invention further relates to a method of treating allergic reactions in a patient, which comprises co-administering to said patient an effective antihistaminic amount of antihistamine of Formula I and an effective p-glycoprotein inhibiting amount of a p-glycoprotein inhibitor. The present invention also relates composition comprising an effective antihistaminic amount of a piperidinoalkanol antihistamine of Formula I and an effective p-glycoprotein inhibiting amount of a p-glycoprotein inhibitor.

DETAILED DESCRIPTION OF THE INVENTION

The present invention provides a method of enhancing bioavailability of a piperidinoalkanol antihistamine of Formula I Formula I

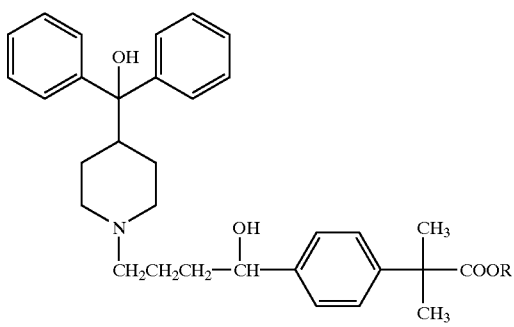

wherein
R is hydrogen or $C_1$–$C_6$ alkyl,
or a pharmaceutically acceptable salt or an individual optical isomer thereof.

As used herein, the term "$C_1$–$C_6$ alkyl" refers to a saturated hydrocarbyl radical of straight or branched chain configuration of from 1 to 6 carbon atoms. Specifically included within the scope of the term "$C_1$–$C_6$ alkyl" are the hydrocarbyl radicals methyl, ethyl, propyl, isopropyl, butyl, sec-butyl, isobutyl, tert-butyl, pentyl, hexyl, and the like. One skilled in the art would immediately recognize and appreciate that the compounds of Formula I possess a chiral center and as such exist in stereoisomeric forms. The present invention applies to the racemic mixture of these stereoisomeric forms as well as to the isolated individual stereoisomers. The individual stereoisomers can be isolated from the racemic mixture by separation techniques which are well known and appreciated in the art including chromatographic methods and selective crystallization techniques.

The compounds of Formula I may exist in their free form or as pharmaceutically acceptable salts. Pharmaceutically acceptable salts of the compounds of Formula I are those of any suitable inorganic or organic acid. Examples of suitable inorganic acids include hydrochloric, hydrobromic, sulfuric, and phosphoric acids. Examples of suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, 4-hydroxybenzoic, anthranillic, cinnamic, salicylic, 4-aminosalicylic, 2-phenoxybenzoic, 2-acetoxybenzoic, mandelic acid, and sulfonic acids, such as, methanesulfonic, ethanesulfonic, and β-hydroxyethanesulfonic acid. Nontoxic salts of the compounds of Formula I formed with inorganic or organic bases are also included within the scope of this invention and include, for example, those of alkali earth metals, for example, calcium and magnesium, light metals of group IIIA, for example, aluminum, organic amines, such as, primary, secondary or tertiary amines, for example, cyclohexylamine, ethylamine, pyridine, methylaminoethanol, and piperazine. The salts of compounds of Formula I may be prepared by conventional means as, for example, by treating a compound of Formula I with an appropriate acid or base. The preferred pharmaceutically acceptable salt for compounds of Formula I is the hydrochloric acid salt.

Compounds of Formula I may be prepared as described in U.S. Pat. No. 4,254,129, which is hereby incorporated by reference in its entirety.

The preferred compound of Formula I is the compound (±)-4-[1-hydroxy-4-[4-(hydroxydiphenylmethyl)-1-piperidinyl]-butyl]-α,α-dimethyl benzeneacetic acid, which is also known as fexofenadine, and its individual stereoisomers. Fexofenadine, as the hydrochloric acid salt, has been recently approved by the United States Food and Drug Administration (FDA) for use as the active ingredient in the antihistamine known as Allegra™. Allegra is indicated for the treatment of seasonal allergic rhinitis with recommended dosing at 60 mg B.I.D.

The present invention provides a method of enhancing bioavailability of the compounds of Formula I. The co-administration of an effective antihistaminic amount of a compound of Fromula I along with an effective p-glycoprotein inhibiting amount of a p-glycoprotein inhibitor provides an enhanced bioavailability for the compounds of Formula I. Bioavailability of a drug is defined as the degree to which a drug becomes available to the target tissue after administration and is conveniently measured as the total amount of drug available systemically. Typically, bioavailability is assessed by measuring the drug concentration in the blood at various points of time after administration of the drug and then integrating the values obtained over time to yield the total amount of drug circulating in the blood. This measurement, called the Area Under the Curve (AUC), is a direct measurement of the bioavailability of the drug. Alternatively, bioavailability may be assessed for fexofenadine by measuring total urine output of fexofenadine, since it is known that fexofenadine is not significantly metabolized after oral administration.

The present invention provides for an enhancement of the bioavailability of the drug of Formula I by co-administration of a p-glycoprotein inhibitor. By co-administration of a compound of Formula I and a p-glycoprotein inhibitor, the total amount of the compound of Formula I is increased over that which would otherwise circulate in the blood in the absence of the p-glycoprotein inhibitor. Thus, co-administration in accordance with the present invention will cause an increase in the AUC of the compound of Formula I over that seen with administration of the compound of Formula I alone.

As used herein, the term "patient" refers to a mammal, such as, for example, a human, mouse, rat, dog, cat, and the like, which is in need of treatment for an allergic reaction. As used herein, the term "allergic reaction" refers to a histamine-mediated allergic disease, such as, for example, seasonal allergic rhinitis, idiopathic urticaria, and the like. Such diseases are generally distinguished by an allergen triggered release of histamine from storage cells in tissues. The released histamine binds certain $H_1$-histamine receptors which results in the manifestation of the well known allergic symptioms such as sneezing, itching skin, itching eyes, rhinorrhea, etc. An antihistamine, such as the compounds of Formula I, will block manifestation of the allergic symptoms caused by release of histamine by blocking the $H_1$-histamine receptors in various tissues in the body, such as in the skin, lungs or the nasal mucosa. Antihistamines, such as the compounds of Formula I, are thus well known and effective treatment for allergic reactions in patients.

Enhancement of bioavailability of a compound of Formula I will provide for a more efficient and effective treatment of the patient since, for a given dose, more compound will be available at the tissue sites at which the antihistamine blocks $H_1$-histamine receptors than in the absence of this enhanced bioavailability.

Administration of the compound of Formula I refers to oral administration. The compound of Formula I may be administered orally in any convenient dosage form including, for example, capsule, tablet, liquid, suspension, and the like.

An effective antihistaminic amount of a compound of Formula I is that amount which is effective in providing an antihistaminic effect in a patient. An effective antihistaminic amount will vary between about 1 mg to about 600 mg of a compound of Formula I as a daily dose depending upon the type of disease to be treated, the degree of severity of the disease, the species of patient to be treated, the dosage regimen, and other factors which are all well within the abilities of one of ordinary skill in the medical arts to evaluate and assess. A preferred amount however will typically be from about 10 mg to about 240 mg, a more preferred amount will typically be from about 20 mg to about 180 mg, and a further preferred amount will typically be from about 40 mg to about 120 mg. The most preferred amount of a compound of Formula I will be 60 mg or 120 mg. The above amounts of a compound of Formula I can be administered from once to multiple times per day. Typically, doses will be administered on a regimen requiring one, two or three doses per day with one and two being the preferred. The more preferred doseage and regimen will be 40 mg twice per day, 60 mg twice per day, 80 mg twice per day, 80 mg once daily, 120 mg once daily, and 180 mg once daily with the most preferred being 60 mg twice per day and 120 mg once daily.

As used herein, the term "p-glycoprotein inhibitor" refers to organic compounds which inhibit the activity of the p-glycoprotein mediated active transport system present in the gut. This transport system actively transports drugs which have been absorbed from the intestinal lumen and into the gut epithelium back out into the lumen. Inhibition of this p-glycoprotein mediated active transport system will cause less drug to be transported back into the lumen and will thus increase the net drug transport across the gut epithelium and will increase the amount of drug ultimately available in the blood.

Various p-glycoprotein inhibitors are well known and appreciated in the art. These include, water soluble vitamin E; polyethylene glycol; poloxamers including Pluronic F-68; Polyethylene oxide; polyoxyethylene castor oil derivatives including Cremophor EL and Cremophor RH 40; Chrysin, (+)-Taxifolin; Naringenin; Diosmin; Quercetin; and the like.

Polyethylene glycols (PEGs) are liquid and solid polymers of the general formula $H(OCH_2CH_2)_nOH$, where n is greater than or equal to 4, having various average molecular weights ranging from about 200 to about 20000. PEGs are also known as α-hydro-ω-hydroxypoly-(oxy-1,2-ethanediyl)polyethylene glycols. For example, PEG 200 is a polyethylene glycol wherein the average value of n is 4 and the average molecular weight is from about 190 to about 210. PEG 400 is a polyethylene glycol wherein the average value of n is between 8.2 and 9.1 and the average molecular weight is from about 380 to about 420. Likewise, PEG 600, PEG 1500 and PEG 4000 have average values of n of 12.5–13.9, 29–36 and 68–84, respectively, and average molecular weights of 570–630, 1300–1600 and 3000–3700, respectively, and PEG 1000, PEG 6000 and PEG 8000 have average molecular weights of 950–1050, 5400–6600, and 7000–9000, respectively. Polyethylene glycols of varying average molecular weight of from 200 to 20000 are well known and appreciated in the art of pharmaceutical science and are readily available.

The preferred polyethylene glycols for use in the instant invention are polyethylene glycols having an average molecular weight of from about 200 to about 20,000. The more preferred polyethylene glycols have an average molecular weight of from about 200 to about 8000. More specifically, the more preferred polyethylene glycols for use in the present invention are PEG 200, PEG 400, PEG 600, PEG 1000, PEG 1450, PEG 1500, PEG 4000, PEG 4600, and PEG 8000. The most preferred polyethylene glycols for use in the instant invention is PEG 400, PEG 1000, PEG 1450, PEG 4600 and PEG 8000.

Polysorbate 80 is an oleate ester of sorbitol and its anhydrides copolymerized with approximately 20 moles of ethylene oxide for each mole of sorbitol and sorbitol anhydrides. Polysorbate 80 is made up of sorbitan mono-9-octadecanoate poly(oxy-1,2-ethandiyl) derivatives. Polysorbate 80, also known as Tween 80, is well known and appreciated in the pharmaceutical arts and is readily available.

Water-soluble vitamin E, also known as d-α-tocopheryl polyethylene glycol 1000 succinate [TPGS], is a water-soluble derivative of natural-source vitamin E. TPGS may be prepared by the esterification of the acid group of crystalline d-α-tocopheryl acid succinate by polyethylene glycol 1000. This product is well known and appreciated in the pharmaceutical arts and is readily available. For example, a water-soluble vitamin E product is available commercially from Eastman Corporation as Vitamin E TPGS.

Naringenin is the bioflavonoid compound 2,3-dihydro-5,7-dihydroxy-2-(4-hydroxyphenyl)-4H-1-benzopyran-4-one and is also known as 4',5,7-trihydroxyflavanone. Naringenin is the aglucon of naringen which is a natural product found in the fruit and rind of grapefruit. Naringenin is readily available to the public from commercial sources.

Quercetin is the bioflavonoid compound 2-(3,4-dihydroxyphenyl)-3,5,7-trihydroxy-4H-1-benzopyran-4-one and is also known as 3,3',4',5,7-pentahydroxyflavone. Quercetin is the aglucon of quercitrin, of rutin and of other glycosides. Quercetin is readily available to the public from commercial sources.

Diosmin is the naturally occurring flavonic glycoside compound 7-[[6-O-6-deoxy-α-L-mannopyranosyl)-β-D-glucopyranosyl]oxy]-5-hydroxy-2-(3-hydroxy-4-methoxyphenyl)-4H-1-benzopyran-4-one. Diosmin can be isolated from various plant sources including citrus fruits. Diosmin is readily available to the public from commercial sources.

Chrysin is the naturally occurring compound 5,7-dihydroxy-2-phenyl-4H-1-benzopyran-4-one which can be isolated from various plant sources. Chrysin is readily available to the public from commercial sources.

Poloxamers are α-hydro-ω-hydroxypoly(oxyethylene) poly(oxypropylene) poly(oxyethylene) block copolymers. Poloxamers are a series of closely related block copolymers of ethylene oxide and propylene oxide conforming to the general formula $HO(C_2H_4O)_a(C_3H_6O)_b(C_2H_4O)_aH$. For example, poloxamer 124 is a liquid with "a" being 12, "b" being 20, and having an average molecular weight of from about 2090 to about 2360; poloxamer 188 is a solid with "a" being 80, "b" being 27, and having an average molecular weight of from about 7680 to about 9510; poloxamer 237 is a solid with "a" being 64, "b" being 37, and having an average molecular weight of from about 6840 to about 8830; poloxamer 338 is a solid with "a" being 141, "b" being 44, and having an average molecular weight of from about 12700 to about 17400; and poloxamer 407 is a solid with "a" being 101, "b" being 56, and having an average molecular weight of from about 9840 to about 14600. Poloxamers are well known and appreciated in the pharmaceutical arts and are readily available commercially. For example, Pluronic F-68 is a commercially available poloxamer from BASF Corp. The preferred poloxamers for use in the present invention are those such as poloxamer 188, Pluronic F-68, and the like.

Polyoxyethylene castor oil derivatives are a series of materials obtained by reacting varying amounts of ethylene oxide with either castor oil or hydrogenated castor oil. These polyoxyethylene castor oil derivatives are well known and appreciated in the pharmaceutical arts and several different types of material are commercially available, including the Cremophors available from BASF Corporation. Polyoxyethylene castor oil derivatives are complex mixtures of various hydrophobic and hydrophilic components. For example, in polyoxyl 35 castor oil (also known as Cremophor EL), the hydrophobic constituents comprise about 83% of the total mixture, the main component being glycerol polyethylene glycol ricinoleate. Other hydrophobic constituents include fatty acid esters of polyethylene glycol along with some unchanged castor oil. The hydrophilic part of polyoxyl 35 castor oil (17%) consists of polyethylene glycols and glyceryl ethoxylates.

In polyoxyl 40 hydrogenated castor oil (Cremophor RH 40) approximately 75% of the components of the mixture are hydrophobic. These comprise mainly fatty acid esters of glycerol polyethylene glycol and fatty acid esters of polyethylene glycol. The hydrophilic portion consists of polyethylene glycols and glycerol ethoxylates. The preferred polyoxyethylene castor oil derivatives for use in the present invention are polyoxyl 35 castor oil, such as Cremophor EL, and polyoxyl 40 hydrogenated castor oil, such as Cremophor RH 40. Cremophor EL and Cremophor RH 40 are commercially available from BASF Corporation.

Polyethylene oxide is a nonionic homopolymer of ethylene oxide conforming to the general formula $(OCH_2CH_2)_n$ in which n represents the average number of oxyethylene groups. Polyethylene oxides are available in various grades which are well known and appreciated by those in the pharmaceutical arts and several different types of material are commercially available. The preferred grade of polyethylene oxide is NF and the like which are commercially available.

(+)-Taxifolin is (2R-trans)-2-(3,4-dihydroxyphenyl)-2,3-dihydro-3,5,7-trihydroxy-4H-1-benzopyran-4-one. Other common names for (+)-taxifolin are (+)-dihydroquercetin; 3,3', 4', 5,7-pentahydroxy-flavanone; diquertin; taxifoliol; and distylin. (+)-Taxifolin is well know and appreciated in the art of pharmaceutical arts and is readily available commercially.

The preferred p-glycoprotein inhibitor for use in the present invention are water soluble vitamin E, such as vitamin E TPGS, and the polyethylene glycols. Of the polyethylene glycols, the most preferred p-glycoprotein inhibitors are PEG 400, PEG 1000, PEG 1450, PEG 4600 and PEG 8000.

Administration of a p-glycoprotein inhibitor may be by any route by which the p-glycoprotein inhibitor will be bioavailable in effective amounts including oral and parenteral routes. Although oral administration is preferred, the p-glycoprotein inhibitors may also be administered intravenously, topically, subcutaneously, intranasally, rectally, intramuscularly, or by other parenteral routes. When administered orally, the p-glycoprotein inhibitor may be administered in any convenient dosage form including, for example, capsule, tablet, liquid, suspension, and the like.

An effective p-glycoprotein inhibiting amount of a p-glycoprotein inhibitor is that amount which is effective in providing inhibition of the activity of the p-glycoprotein mediated active transport system present in the gut. An effective p-glycoprotein inhibiting amount will vary between about 5 mg to about 1000 mg of p-glycoprotein inhibitor as a daily dose depending upon the particular p-glycoprotein inhibitor selected, the species of patient to be treated, the dosage regimen, and other factors which are all well within the abilities of one of ordinary skill in the medical arts to evaluate and assess. A preferred amount however will typically be from about 50 mg to about 500 mg, and a more preferred amount will typically be from about 100 mg to about 500 mg. The above amounts of a p-glycoprotein inhibitor can be administered from once to multiple times per day. Typically for oral dosing, doses will be administered on a regimen requiring one, two or three doses per day with one and two being the preferred.

Where water soluble vitamin E or a polyethylene glycol is selected as the p-glycoprotein inhibitor, a preferred amount will typically be from about 5 mg to about 1000 mg, a more preferred amount will typically be from about 50 mg to about 500 mg, and a further preferred amount will typically be from about 100 mg to about 500 mg. The most preferred amount of water soluble vitamin E or a polyethylene glycol will be from about 200 mg to about 500 mg. The above amounts of water soluble vitamin E or polyethylene glycol can be administered from once to multiple times per day. Typically, doses will be administered on a regimen requiring one, two or three doses per day with one and two being preferred.

As used herein, the term "co-administration" refers to administration to a patient of both a compound of Formula I and a p-glycoprotein inhibitor so that the pharmacologic effect of the p-glycoprotein inhibitor in inhibiting p-glycoprotein mediated transport in the gut is manifest at the time at which the compound of Formula I is being absorbed from the gut. Of course, the compound of Formula I and the p-glycoprotein inhibitor may be administered at different times or concurrently. For example, the p-glycoprotein inhibitor may be administered to the patient at a time prior to administration of the compound of Formula I so as to pre-treat the patient in preparation for dosing with the compound of Formula I. Furthermore, it may be convenient for a patient to be pre-treated with the p-glycoprotein inhibitor so as to achieve steady state levels of p-glycoprotein inhibitor prior to administration of the first dose of the compound of Formula I. It is also contemplated that the compound of Formula I and the p-glycoprotein inhibitor may be administered essentially concurrently either in separate dosage forms or in the same oral dosage form.

The present invention further contemplates that the compound of Formula I and the p-glycoprotein inhibitor may be administered in separate dosage forms or in the same combination oral dosage form. Co-administration of the compound of Formula I and the p-glycoprotein inhibitor may conveniently be accomplished by oral administration of a combination dosage form containing both the compound of Formula I and the p-glycoprotein inhibitor.

Thus, an additional embodiment of the present invention is a combination pharmaceutical composition for oral administration comprising an effective antihistaminic amount of a compound of Formula I (the antihistamine) and an effective p-glycoprotein inhibiting amount of a p-glycoprotein inhibitor (the inhibitor). This combination oral dosage form may provide for immediate release of both the compound of Formula I and the p-glycoprotein inhibitor or may provide for sustained release of one or both of the compound of Formula I and the p-glycoprotein inhibitor. One skilled in the art would readily be able to determine the appropriate properties of the combination dosage form so as to achieve the desired effect of co-administration of the compound of Formula I and the p-glycoprotein inhibitor.

The antihistamine and the inhibitor may be administered alone or in the form of a pharmaceutical composition in admixture or otherwise in association with one or more pharmaceutically acceptable carriers or excipients, the proportion and nature of which are determined by the solubility and chemical properties of the antihistamine and inhibitior selected, the dosage regimen desired and standard pharmaceutical practice. The antihistamines, while effective themselves, may be formulated and administered in the form of their pharmaceutically acceptable acid addition salts, such as the hydrochloride, for purposes of stability, convenience of cystallization, increased solubility and the like. One form of the pharmaceutical composition according to the present invention is a combination pharmaceutical composition where both the antihistamine and the inhibitor are present in the same dosage form.

The pharmaceutical composition may be prepared in a manner well known and appreciated in the pharmaceutical art. The carrier or excipient is pharmacologically inert and may be a solid, semi-solid, or liquid material which can serve as a vehicle or medium for the antihistamine and the inhibitor. Suitable carriers and excipients are well known in the art. The pharmaceutical compositon may be adapted for oral administration in the form of a tablet, capsule, liquid, syrup, wafer, chewing gum, suspension, or the like. These preparations may contain at least 4% of active ingredient, i.e., the percent by weight of the antihistamine and the inhibitor, but may conveniently be varied depending upon the particular form so that the active ingredients make up from about 4% to about 70% of the weight of the unit dosage form.

Tablets, pills, capsules, and the like may contain one or more of the following carriers or excipients: binders such as microcrystalline cellulose, gum tragacanth or gelatin; excipients such as starch or lactose; surfactants such as polysorbate 80, and the like; disintegrating agents such as alginic acid, Primogel™, corn starch, sodium bicarbonate, calcium bicarbonate and the like; lubricants such as magnesium stearate or Sterotex™; glidants such as colloidal silicon dioxide; sweetening agents such as sucrose or saccharin; flavoring agent such as peppermint, methyl salicylate or orange flavoring. Capsules may contain, in addition to the ingredients listed above for tablets, a liquid carrier such as polyethylene glycol or a fatty oil. Tablets and capsules may contain other various carriers and excipients which modify the physical form of the dosage unit, for example, as coatings. Thus, tablets may be coated with sugar, shellac, or other enteric coating agents. A syrup may contain, in addition to the active ingredients, sterile water, sucrose as a sweetening agent, preservatives, dyes, and colorings and flavors. Materials used in preparing these various compositions should be pharmaceutically pure and non-toxic in the amounts used.

For purposes of parenteral administration, the inhibitor may be incorporated into a solution or suspension. These preparations should contain at least 0.1% of the active ingredient but may be varied from about 0.1% to about 50% by weight thereof. The amount of the inhibitor should be adjusted in such compositions so that an a suitable dosage will be obtained upon administration.

The solutions or suspensions may also include one or more of the following adjuvants: sterile diluents such as water, saline, fixed oils, polyethylene glycols, glycerine, propylene glycols or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates; agents for the adjustment of tonicity such as sodium chloride or dextrose. The parenteral preparations may be enclosed in ampules, disposable syringes or multiple dosage vials made of glass or plastic.

More particularly, the combination pharmaceutical composition may be in the form of a tablet, a capsule, a liquid, a suspension, a syrup, and the like. The combination pharmaceutical composition, including in tablet form, may be a simple admixture of the antihistamine, the inhibitor, and any necessary and appropriate carriers and excipients. Alternatively, the composition may be in the form of an admixture of various heterogeneous pellets, beads or other heterogeneous particles which provide an appropriate formulation. In addition, the pharmaceutical composition may be in the form of a multiple compression tablet such as a multilayered tablet or a compression-coated tablet.

Combination pharmaceutical compositions made up of heterogeneous pellets, beads or particles (hereinafter referred to as "heterogeneous pellets"), or made up of multiple compression tablets, are useful for administration of pharmaceutical compositions which provide for different release characteristics for the antihistamine and inhibitor. For example, these compositions may provide for an immediate release of the inhibitor and a sustained release of the antihistamine, or vice versa. These compositions are prepared according to standard techniques which are well known and appreciated in the art such as those described in U.S. Pat. No. 4,996,061 which is hereby incorporated by reference in its entirety.

The following examples illustrate a particularly preferred embodiment of the present invention. These examples are illustrative only and are not intended to limit the scope of the invention in any way.

EXAMPLE 1

Effect of PEG 400 on the Bioavailabilty of Fexofenadine in the Dog

The effect of polyethylene glycol 400 (PEG 400) on the bioavailability of fexofenadine was determined in two fasted, male beagle dogs. Treatment A consisted of oral administration of one 120 mg fexofenadine hydrochloride sustained release (SR) tablet, and treatment B consisted of oral administration of one SR tablet together with a capsule with 0.5 mL PEG 400 given at −1, 0, 2, 4, 6, and 8 hours before and after the SR tablet. Treatment A was given 10 or 17 days prior to Treatment B. The plasma concentrations of fexofenadine were analyzed to determine relative bioavailability of fexofenadine with and without concomitant treatment with PEG 400.

A mean 2-fold increase in plasma concentrations (Table I) occurred when PEG 400 was co-administered with fexofenadine. This doubling of fexofenadine bioavailability is also shown in FIG. 1, which illustrates the increase in mean plasma concentrations produced during co-administration.

TABLE I

Plasma Concentrations of Fexofenadine in Dogs Given a 120 mg Fexofenadine SR Tablet Dose Alone or with 0.5 mL PEG-400 Capsule Doses

| Dose Condition | Time (Hours) | Fexofenadine Concentration (ng/mL) | | |
|---|---|---|---|---|
| | | Dog Number 7645 | 3181 | Mean |
| Fexofenadine Alone | 0 | 0 | 0 | 0 |
| | 0.5 | 192.93 | 221.88 | 207.41 |
| | 1 | 523.96 | 1196.64 | 860.30 |
| | 1.5 | 748.57 | 1537.07 | 1142.82 |
| | 2 | 1617.8 | 2088.09 | 1852.95 |
| | 3 | 2316.21 | 1865.81 | 2091.01 |
| | 5 | 2364.18 | 793.03 | 1578.61 |
| | 7 | 1170.93 | 276.88 | 723.91 |
| | 9 | 880.07 | 184.32 | 532.20 |
| | 12 | 350.02 | 91.25 | 220.64 |
| | 14 | 274.33 | 69.49 | 171.91 |
| | 22 | 110.33 | 28.95 | 69.64 |
| | 24 | 97.87 | 34.68 | 66.28 |
| Fexofenadine + PEG-400 | 0 | 0 | 0 | 0 |
| | 0.5 | 783.93 | 154.38 | 469.16 |
| | 1 | 5866.28 | 687.3 | 3276.79 |
| | 1.5 | 7574.3 | 820.16 | 4197.23 |
| | 2 | 10116.53 | 1277.5 | 5697.02 |
| | 3 | 9794.6 | 3736.69 | 6765.65 |
| | 5 | 4794.46 | 1342.66 | 3068.56 |
| | 7 | 1400.87 | 565.14 | 983.01 |
| | 9 | 890.27 | 240.76 | 565.52 |
| | 12 | 585.41 | 139.86 | 362.64 |
| | 14 | 293.91 | 82.72 | 188.32 |
| | 22 | 108.74 | 59.66 | 84.20 |
| | 24 | 93.73 | 51.54 | 72.64 |

EXAMPLE 2

Effect of Water Suluble Vitamin E on the Bioavailability of Fexofenadine in the Dog The effect of water soluble vitamin E (d-α-tocopheryl polyethylene glycol succinate) on the bioavailability of fexofenadine was determined in two fasted, male beagle dogs in two-way crossover experimental design. Treatment A consisted of oral administration of an aqueous solution of a 1 mg/kg dose of $^{14}$C-labeled fexofenadine alone, and Treatment B consisted of oral administration of an aqueous solution of the same dose of $^{14}$C-labeled fexofenadine and a 10 IU/Kg dose of water soluble vitamin E. Treatments were given in the opposing order of a crossover design in the two dogs, and a on week washout period occurred between treatments. The radioactivity in plasma and urine was analyzed and is known to represent unchanged fexofenadine in the dog. The results showed a 50% increase in plasma $^{14}$C AUC occurred when water soluble vitamin E was co-administered with $^{14}$C fexofenadine (Table II). That is, the bioavailability of fexofenadine was increased 50% by water soluble vitamin E. FIG. 2 illustrates the increase in mean plasma concentrations caused by co-administration of water soluble vitamin E.

TABLE II

Plasma Concentrations of [$^{14}$C]Fexofenadine in Dogs Given a 1 mg/kg [$^{14}$C]Fexofenadine Oral Solution Dose Alone or with 10 IU/kg Water Soluble Vitamin E

| Dose Condition | Time (Hours) | [$^{14}$C]Fexofenadine Concentration (ng equiv/mL) | | |
|---|---|---|---|---|
| | | Dog Number 7645 | 3181 | Mean |
| Fexofenadine Alone | 0 | 0 | 0 | 0 |
| | 0.5 | 509 | 829 | 669 |
| | 1 | 546 | 673 | 609.5 |
| | 1.5 | 815 | 743 | 779 |
| | 2 | 924 | 559 | 741.5 |
| | 3 | 882 | 386 | 634 |
| | 5 | 330 | 128 | 229 |
| | 7 | 155 | 81 | 118 |
| | 9 | 82 | 54 | 68 |
| | 12 | 40 | 26 | 33 |
| | 14 | 33 | 18 | 25.5 |
| | 22 | 15 | 5 | 10 |
| | 24 | 9 | 8 | 8.5 |
| Fexofenadine + WS Vit E | 0 | 0 | 0 | 0 |
| | 0.5 | 853 | 1472 | 1162.5 |
| | 1 | 1721 | 1098 | 1409.5 |
| | 1.5 | 1974 | 805 | 1389.5 |
| | 2 | 1515 | 572 | 1043.5 |
| | 3 | 1104 | 558 | 831 |
| | 5 | 230 | 257 | 243.5 |
| | 7 | 163 | 120 | 141.5 |
| | 9 | 90 | 73 | 81.5 |
| | 12 | 51 | 40 | 45.5 |
| | 14 | 48 | 31 | 39.5 |
| | 22 | 14 | 11 | 12.5 |
| | 24 | 10 | 13 | 11.5 |

The increase in absorption and bioavailability of fexofenadine that occurred with concomitant administration of water soluble vitamin E was also evident from the urinary excretion of $^{14}$C fexofenadine in urine, which increased a mean of 3-fold (Table II).

TABLE III

Percent of [$^{14}$C]Fexofenadine Excreted in Urine of Dogs Given a 1 mg/kg Oral [$^{14}$C]Fexofenadine Hydrochloride Dose Without or With Water Soluble Vitamin E Excipient.

| Dog Number | Without Excipient (% Dose) | With Excipient (% Dose) | Ratio |
|---|---|---|---|
| 7645 | 2.38 | 9.88 | 4.2 |
| 3181 | 2.80 | 4.79 | 1.7 |
| Mean | 2.59 | 7.34 | 3.0 |

EXAMPLE 3

Effect of PEG 1000 on the Bioavailabilty of Fexofenadine in the Dog

The effect of polyethylene glycol 1000 (PEG 1000) on the bioavailability of fexofenadine was determined in two fasted, male beagle dogs. Treatment A consisted of oral administration of one 120 mg fexofenadine hydrochloride sustained release (SR) tablet, and treatment B consisted of oral administration of one SR tablet together with a capsule containing 0.5 g PEG 1000 dissolved in 2.5 mL water given at −1, −0.1, and 4 hours before and after the SR tablet. Treatment A was given two months prior to Treatment B. The plasma concentrations of fexofenadine were analyzed to determine relative bioavailability of fexofenadine with and without concomitant treatment with PEG 1000.

A mean 2-fold increase in plasma concentrations [AUC (0-24h) values calculated from the concentrations shown in Table IV] occurred when PEG 1000 was co-administered with fexofenadine. The peak concentration was increased a mean of 3-fold. This increased bioavailability in the presence of PEG 1000 is evident in the graph of mean plasma fexofenadine concentrations (FIG. 3).

TABLE IV

Plasma Concentrations of Fexofenadine in Dogs Given a 120 mg Fexofenadine SR Tablet Dose Alone or with 0.5 g PEG-1000 Capsule Solution Doses

| Dose Condition | Time (Hours) | Fexofenadine Concentration (ng/mL) | | |
|---|---|---|---|---|
| | | Dog Number | | |
| | | 7645 | 3181 | Mean |
| Fexofenadine Alone | 0 | 0 | 0 | 0 |
| | 0.5 | 192.93 | 221.88 | 207.41 |
| | 1 | 523.96 | 1196.64 | 860.30 |
| | 1.5 | 748.57 | 1537.07 | 1142.82 |
| | 2 | 1617.8 | 2088.09 | 1852.95 |
| | 3 | 2316.21 | 1865.81 | 2091.01 |
| | 5 | 2364.18 | 793.03 | 1578.61 |
| | 7 | 1170.93 | 276.88 | 723.91 |
| | 9 | 880.07 | 184.32 | 532.20 |
| | 12 | 350.02 | 91.25 | 220.64 |
| | 14 | 274.33 | 69.49 | 171.91 |
| | 22 | 110.33 | 28.95 | 69.64 |
| | 24 | 97.87 | 34.68 | 66.28 |
| Fexofenadine + PEG-1000 | 0 | 0 | 0 | 0 |
| | 0.5 | 15.28 | 147.24 | 81.31 |
| | 1 | 669.27 | 473.48 | 571.38 |
| | 1.5 | 1133.02 | 1687.98 | 1410.50 |
| | 2 | 4541.31 | 3963.22 | 4252.27 |
| | 3 | 7695.42 | 5595.32 | 6645.37 |
| | 5 | 3398.34 | 2035.32 | 2716.83 |
| | 7 | 1320.73 | 857.89 | 1089.31 |
| | 9 | 784.42 | 377.1 | 580.76 |
| | 12 | 315.74 | 202.89 | 259.32 |
| | 24 | 109.69 | 112.75 | 111.22 |

We claim:
1. A method for enhancing bioavailability of a piperidinoalkanol antihistamine of the formula

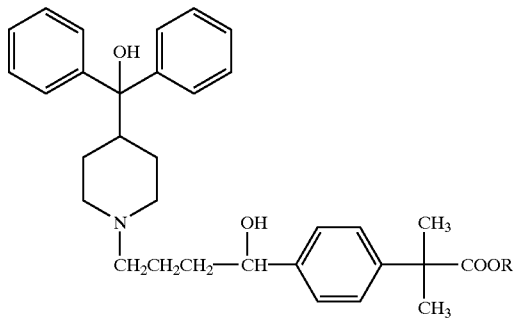

wherein
R is hydrogen or $C_1$–$C_6$ alkyl,
or a pharmaceutically acceptable salt or an individual optical isomer thereof, in a patient which comprises co-administering to said patient an effective antihistaminic amount of said piperidinoalkanol antihistamine and an effective p-glycoprotein inhibiting amount of a p-glycoprotein inhibitor.
2. A method of claim 1 wherein the antihistamine is fexofenadine, or a pharmaceutically acceptable salt thereof.
3. A method of claim 2 wherein the p-glycoprotein inhibitor is selected from the group consisting of water soluble vitamin E and polyethylene glycols.
4. A method of claim 3 wherein the p-glycoprotein inhibitor is water soluble vitamin E or is selected from the group consisting of PEG 400, PEG 1000, PEG 1450, PEG 4600 and PEG 8000.
5. A method of claim 4 wherein the p-glycoprotein inhibitor is water soluble vitamin E.
6. A method of claim 4 wherein the p-glycoprotein inhibitor is PEG 1000.
7. A method of treating allergic reactions in a patient which comprises co-administering to said patient an effective antihistaminic amount of a piperidinoalkanol antihistamine of the formula

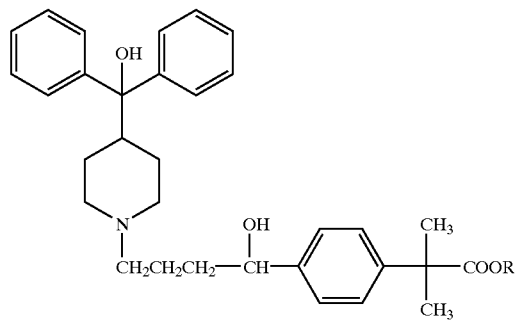

wherein
R is hydrogen or $C_1$–$C_6$ alkyl,
or a pharmaceutically acceptable salt or an individual optical isomer thereof, and an effective p-glycoprotein inhibiting amount of a p-glycoprotein inhibitor.
8. A method of claim 7 wherein the antihistamine is fexofenadine, or a pharmaceutically acceptable salt thereof.
9. A method of claim 8 wherein the p-glycoprotein inhibitor is selected from the group consisting of water soluble vitamin E and polyethylene glycols.
10. A method of claim 9 wherein the p-glycoprotein inhibitor is water soluble vitamin E or is selected from the group consisting of PEG 400, PEG 1000, PEG 1450, PEG 4600 and PEG 8000.
11. A method of claim 10 wherein the p-glycoprotein inhibitor is water soluble vitamin E.
12. A method of claim 10 wherein the p-glycoprotein inhibitor is PEG 1000.
13. A pharmaceutical composition comprising an effective antihistaminic amount of a piperidinoalkanol antihistamine of the formula

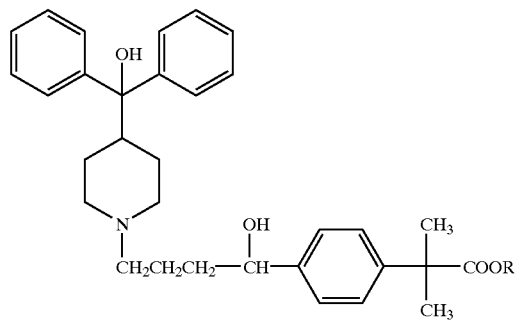

wherein
R is hydrogen or $C_1$–$C_6$ alkyl,
or a pharmaceutically acceptable salt or an individual optical isomer thereof, and an effective p-glycoprotein inhibiting amount of a p-glycoprotein inhibitor.

14. A composition of claim 13 wherein the antihistamine is fexofenadine, or a pharmaceutically acceptable salt thereof.

15. A composition of claim 14 wherein the p-glycoprotein inhibitor is selected from the group consisting of water soluble vitamin E and polyethylene glycols.

16. A composition of claim 15 wherein the p-glycoprotein inhibitor is water soluble vitamin E or is selected from the group consisting of PEG 400, PEG 1000, PEG 1450, PEG 4600 and PEG 8000.

17. A composition of claim 16 wherein the p-glycoprotein inhibitor is water soluble vitamin E.

18. A composition of claim 16 wherein the p-glycoprotein inhibitor is PEG 1000.

19. The use of a composition in the manufacture of a medicament for enhancing bioavailability of a piperidinoalkanol antihistamine of the formula

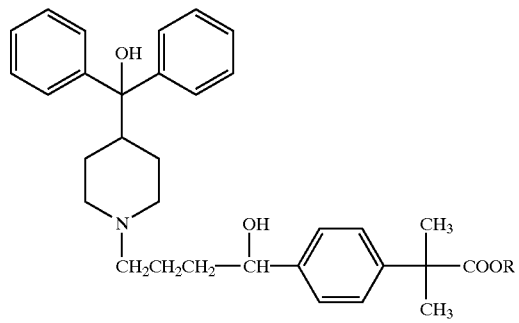

wherein

R is hydrogen or $C_1$–$C_6$ alkyl, or a pharmaceutically acceptable salt or an individual optical isomer thereof, wherein said composition comprises an effective antihistaminic amount of said piperidinoalkanol antihistamine and an effective p-glycoprotein inhibiting amount of a p-glycoprotein inhibitor.

20. A use of claim 19 wherein the antihistamine is fexofenadine, or a pharmaceutically acceptable salt thereof.

21. A use of claim 20 wherein the p-glycoprotein inhibitor is selected from the group consisting of water soluble vitamin E and polyethylene glycols.

22. A use of claim 21 wherein the p-glycoprotein inhibitor is water soluble vitamin E or is selected from the group consisting of PEG 400, PEG 1000, PEG 1450, PEG 4600 and PEG 8000.

23. A use of claim 22 wherein the p-glycoprotein inhibitor is water soluble vitamin E.

24. A use of claim 22 wherein the p-glycoprotein inhibitor is PEG 1000.

25. The use of a composition in the manufacture of a medicament allergic reactions in a patient wherein said composition comprises an effective antihistaminic amount of a piperidinoalkanol antihistamine of the formula

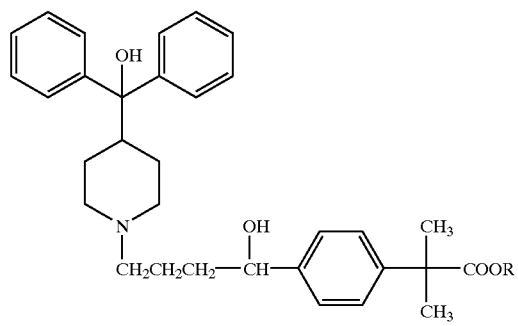

wherein

R is hydrogen or $C_1$–$C_6$ alkyl, or a pharmaceutically acceptable salt or an individual optical isomer thereof, and an effective p-glycoprotein inhibiting amount of a p-glycoprotein inhibitor.

26. A use of claim 25 wherein the antihistamine is fexofenadine, or a pharmaceutically acceptable salt thereof.

27. A use of claim 26 wherein the p-glycoprotein inhibitor is selected from the group consisting of water soluble vitamin E and polyethylene glycols.

28. A use of claim 27 wherein the p-glycoprotein inhibitor is water soluble vitamin E or is selected from the group consisting of PEG 400, PEG 1000, PEG 1450, PEG 4600 and PEG 8000.

29. A use of claim 28 wherein the p-glycoprotein inhibitor is water soluble vitamin E.

30. A use of claim 28 wherein the p-glycoprotein inhibitor is PEG 1000.

* * * * *